United States Patent [19]

Chandra et al.

[11] 4,005,046

[45] Jan. 25, 1977

[54] CATALYSTS AND CARRIERS THEREFOR

[75] Inventors: Grish Chandra, Penarth; Brian John Griffiths, Coytrahen, near Bridgend, Wales

[73] Assignee: Dow Corning Limited, Barry, Wales

[22] Filed: Nov. 6, 1975

[21] Appl. No.: 629,268

[30] Foreign Application Priority Data

Nov. 12, 1974 United Kingdom ............ 49028/74

[52] U.S. Cl. .............................. 252/428; 252/430; 252/429 R; 252/431 R; 252/431 N
[51] Int. Cl.$^2$ ........................................ B01J 31/02
[58] Field of Search ............... 252/428, 429 R, 430, 252/431 N

[56] References Cited

UNITED STATES PATENTS

| | | | |
|---|---|---|---|
| 3,024,126 | 3/1962 | Brown | 252/428 |
| 3,722,181 | 3/1973 | Kirkland et al. | 252/428 X |
| 3,775,452 | 11/1973 | Karstedt | 252/429 R |
| 3,892,678 | 7/1975 | Halasz et al. | 252/428 |

*Primary Examiner*—Winston A. Douglas
*Assistant Examiner*—John F. Niebling
*Attorney, Agent, or Firm*—Robert F. Fleming, Jr.

[57] ABSTRACT

A catalyst carrier substance which can be obtained by reacting an inorganic particulate solid having surface hydroxyl groups with an organosilicon compound containing sulphur. The carrier may be converted to a supported catalyst by reaction with a compound or complex of platinum or rhodium. The catalysts can be recovered and recycled and are useful in hydrogenation, hydroformylation and oligomerization reactions. They are of particular interest with respect to hydrosilylation reactions.

6 Claims, No Drawings

CATALYSTS AND CARRIERS THEREFOR

This invention relates to catalyst carrier substances, to catalysts supported thereon and to the use of such catalysts in hydrosilylation reactions.

According to the invention there is provided a catalyst carrier substance which is an inorganic, particulate solid having chemically bonded to the surface thereof at least one group of the general formula

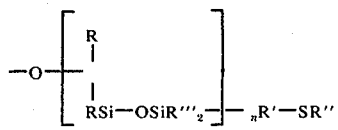

wherein the R substituents are the same or different and each R represents a chlorine atom, a bromine atom, a monovalent radical having from 1 to 8 inclusive carbon atoms and free of aliphatic unsaturation which is a hydrocarbon radical, a halogenated hydrocarbon radical, or an oxyhydrocarbon radical, the radical $-NQ_2$, in which each Q represents a hydrogen atom or an alkyl or aryl radical having less than 10 carbon atoms, an oxime radical having less than 14 carbon atoms, or R represents an oxygen atom through which the silicon atom is linked to the surface of the inorganic, particulate solid, R' represents a divalent hydrocarbon radical having from 1 to 16 inclusive carbon atoms, R'' and each R''' represent a monovalent hydrocarbon radical free of aliphatic unsaturation and having from 1 to 8 inclusive carbon atoms, and $n$ is 0 or an integer of from 1 to 20.

In the general formula of the surface-bonded groups the R substituents may be the same or different and each R may be, for example, a chlorine atom, a bromine atom, an alkyl aryl, alkaryl, aralkyl, halogenated alkyl or halogenated aryl radical having from 1 to 8 inclusive carbon atoms, an oxime radical having less than 14 carbon atoms, the radical $-NQ_2$ or an oxyhydrocarbon radical in which the oxygen is present in the form of ether linkages or in ester groups, alkoxy radicals, alkoxyalkoxy radicals or aryloxy radicals. Examples of such radicals are methyl, ethyl, propyl, butyl, 2,4,4-trimethylpentyl, chloromethyl, 3,3,3-trifluoropropyl, cyclohexyl, phenyl, benzyl, tolyl, methoxy, ethoxy, propoxy, n-butoxy, methoxyethoxy, ethoxyethoxy, acetoxy, propionoxy, $-ON=C(C_2H_5)_2$ and $-NHCH_3$. R may also represent an oxygen atom linking the silicon atom and the surface of the inorganic solid. Preferably R represents a methyl radical, a phenyl radical or an alkoxy radical having from 1 to 4 inclusive carbon atoms.

The divalent radical R' may be for example $-CH_2-$,

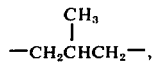

$-(CH_2)_{14}-$ and phenylene, and R'' and each R''' may be for example methyl, ethyl, propyl, n-butyl, n-octyl, cyclohexyl and phenyl. Preferably R' has from 1 to 4 carbon atoms, $n$ is zero, R'' represents an ethyl or a butyl radical and R''' when present represents the methyl radical.

The inorganic particulate solid employed in the catalyst carrier of this invention may be any substance which is susceptible to the attachment of the $-OSi(R_2)(OSiR'''_2)_nR'SR''$ grouping and which has no deleterious effect on the reaction to be catalysed. Such substances will in the unmodified state have surface hydroxyl groups which react with an organosilicon compound to provide the desired surface bonded sulphur-bearing groups. Examples of such particulate solids are silicas e.g. quartz, precipitated silica and silica gel, zeolitic molecular sieve, kaolin, alumina and titania, the preferred solids being the silicas.

The particle size of the particulate solid is not critical. For ease of recovery of the catalyst from liquid reaction residues or products however, the preferred solids are those having a particle size within the range from 5 to 100 mesh British Standard Test Sieve. (B.S.410:1962).

The catalyst carrier substances of this invention can be prepared by reacting an inorganic particulate solid having surface hydroxyl groups with an organosilicon compound of the formula

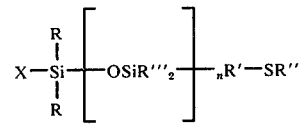

in which R', R'' and R''' and $n$ are as hereinbefore defined, X represents an atom or group reactive with the surface hydroxyl groups of the particulate solid, and each R, which may or may not be reactive with the said surface hydroxyl groups is as hereinbefore defined except that R may not be an oxygen atom.

Examples of X atoms and groups are the chlorine atoms, bromine atoms, hydroxyl radical, alkoxy and alkoxyalkoxy radicals (preferably having less than 6 carbon atoms), acetoxy radicals, $-O-N=C(CH_3)(C_2H_5)$ radical and $-N(CH_3)_2$ radical.

The sulphur-containing organosilicon reactants are in general known materials and may be prepared by known procedures.

In an alternative and more preferred method of preparing certain of the catalyst carrier substances according to this invention the inorganic solid is reacted with a disilazane $$HN[Si(R_2)R'SR'']_2$$

wherein R' and R'' are as hereinbefore defined and each R represents a monovalent radical having from 1 to 8 inclusive carbon atoms and free of aliphatic unsaturation which is a hydrocarbon radical, a halogenated hydrocarbon radical or an oxyhydrocarbon radical.

It is believed that during the reaction the SiN bonds are ruptured and one molecule of the silazane produces two silyl groups for reaction with the hydroxyl groups on the surface of the inorganic solid. The disilazane reactant may be prepared by the reaction of $HN(R_2SiZ)_2$, in which Z represents a monovalent olefinically unsaturated radical, with a thiol R''SH in the presence of a free radical catalyst. Such a process is described in our copending U.S. Application Serial No. 629,269.

According to another method of preparing the catalyst carriers of this invention a compound which is (a)

a silane or siloxane $XSiR_2[-OSiR'''_2]_nZ$, (b) a disilazane $(ZSiR_2)_2NH$ or (c) a cyclic silazane $(ZRSiNH)_m$, in which compounds R, R''' and n are as hereinbefore defined, m is a low number, preferably 3, 4 or 5, X represents an atom or group reactive with the hydroxyl groups on the inorganic solid surface and Z represents a monovalent hydrocarbon radical having olefinic unsaturation, preferably the vinyl radical or allyl radical, is reacted as a first step with the hydroxyl groups on the inorganic solid surface. The product is then reacted with a thiol R''SH in the presence of a suitable catalyst e.g. azo-bisisobutyronitrile whereby the thiol adds to the unsaturated portion of the molecule to form the desired group.

A further method by which the catalyst carriers of this invention may be obtained involves reacting a silane such as $XSiR_2R'Cl$, in which X is e.g. chlorine, methoxy, ethoxy, or acetoxy and R and R' are as hereinbefore defined, with surface hydroxyl groups in the inorganic solid. The product is then reacted with NaSR'' whereby the chlorine atom attached to R' is replaced with SR''.

The reactions between the organosilicon compounds and the inorganic substrate are preferably carried out in the presence of an inert organic solvent, for example toluene, xylene or benzene. In order to expedite the reaction elevated temperatures are desirably employed and preferably the reaction is carried out at temperatures of from about 80° to 140° C under reflux. If desired the reaction may also be expedited by including a suitable catalyst, for example, p-toluene sulphonic acid, dibutyltin diacetate or other silanol condensation catalyst.

The catalyst carriers may be reacted with a compound or complex of platinum or rhodium to form catalysts for hydrosilylation and other reactions. Another aspect of this invention therefore resides in a catalyst comprising an inorganic particulate solid having bonded to the surface thereof a group

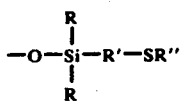

in which R, R' and R'' are as hereinbefore defined and the sulphur atom is bonded co-ordinatively to an atom of Pt or Rh.

Also included within the scope of this invention is a process for preparing a catalyst which comprises reacting a catalyst carrier substance of this invention with a compound or complex of Pt or Rh having a labile ligand. Said reaction may be carried out in most cases by merely contacting the catalyst carrier substances with the Pt or Rh compound at room temperature. Higher temperatures may however, be employed. Where the Pt or Rh compound or complex is a solid the reaction is best performed in the presence of a solvent, e.g. benzene, toluene, xylene, or more preferably, a polar solvent e.g. methanol, ethanol, dioxane and/or water. Examples of preferred compounds and complexes for use in the reaction are $H_2PtCl_6·6H_2O$, $PtBr_2$, $Na_2PtCl_4·4H_2O$, $(NH_4)_2PtCl_4$, $K[Pt(C_2H_4)Cl_3]·H_2O$, $RhCl_3xH_2O$, $Rh_2(CO)_4Cl_2$, $Rh(C_2H_4)_2(AcAc)$, $Rh_2(C_2H_4)_2Cl_2$ and

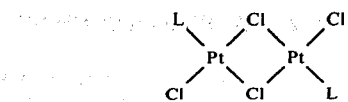

in which L is a ligand, for example an olefin.

The catalysts of this invention can also be prepared by first reacting the sulphur-containing silane, siloxane or silazane with a Pt or Rh compound or complex and thereafter reacting the resulting product with the inorganic particulate solid. The Pt or Rh containing complexes employed in said reaction can be obtained by contacting the appropriate silicon compound and the Pt or Rh compound or complex at temperatures ranging from below normal room temperature to above 150° C. When one of the reactants is liquid the reaction may, if desired, be carried out in the absence of a solvent. Usually, however, it is preferred to perform the reaction in the presence of a polar solvent, for example methanol, ethanol or tetrahydrofuran, or a mixture of a polar solvent and water.

The catalysts of this invention can be employed in hydrogenation, hydroformylation and oligomerisation reactions. They are however, of particular utility for the catalysis of hydrosilylation reactions, that is reactions involving the addition of silicon-bonded hydrogen atoms to organic radicals containing aliphatic unsaturation. Included within the scope of this invention therefore is a process for the preparation of an organosilicon product which comprises reacting in the presence of a catalyst of this invention (i) an organosilicon substance having in the molecule at least one silicon-bonded hydrogen atom and (ii) an organic or organosilicon substance containing aliphatic carbon atoms linked by multiple bonds.

As the organosilicon material (i) there may be employed, for example, one or more silanes or organosiloxanes. Examples of such materials are $HSiCl_3$, $CH_3SiHCl_2$, $C_6H_5SiHCH_3Br$, $(CH_3)_2SiHCl$, $C_2H_5SiH_2Cl$, $CH_3SiH(OCH_3)_2$, methylhydrogen polysiloxanes and copolymers of methylhydrogensiloxane units and, for example, dimethylsiloxane units, trimethylsiloxane units and phenylethylsiloxane units. The nature of the silicon-bonded substituents present in addition to the hydrogen atoms is not critical but normally such substituents will comprise halogen atoms, alkoxy radicals, preferably having less than 6 carbon atoms and monovalent hydrocarbon or halogenated hydrocarbon radicals having from 1 to 18 inclusive carbon atoms.

The compound (ii) containing carbon atoms linked by multiple bonds may be organic, for example, pentene-1-, hexene-2, heptene-1, acetylene, butadiene, vinylacetylene, cyclohexene, styrene, allyl bromide, vinyl acetate, allyl alcohol or an allyl ether of a poly(alkylene oxide). Compound (ii) may also be organosilicon, for example $(CH_3)_2(CH_2=CH)SiCl$, $(CH_2=CHCH_2)_2SiBr_2$, $(CH_2=CH)Si(C_2H_5)_2Cl$, and organosiloxanes and polysiloxanes containing silicon-bonded vinyl and/or allyl radicals. Any remaining silicon-bonded substituents in the unsaturated organosilanes and organosiloxanes may be, for example, halogen atoms, alkoxy radicals having less than 6 carbon atoms and monovalent hydrocarbon or halogenated hydrocarbon radicals having from 1 to 18 inclusive carbon atoms.

The reaction of silicon-bonded hydrogen atoms with unsaturated radicals is well-known and may be employed for the preparation of organofunctional and other organosilicon compounds and in the preparation of elastomeric or resinous organosilicon products. The hydrosilylation reaction may be performed at atmospheric, sub-atmospheric or super-atmospheric pressures, in the presence or absence of solvents, and at temperatures ranging from below 20° C up to and in excess of 150° C.

The catalysts of this invention have the advantage over previously known hydrosilylation catalysts e.g. $2PtCl_6$ that they are easily recovered from reaction residues by decantation or filtration. After recovery the catalysts may be recycled thereby effecting a significant reduction in the cost of chemical processes employing such catalysts. If desired, however, the catalyst may be allowed to remain in the reaction product where, in the case of e.g. an elastomeric or resinous product, it may function as for example an additive or filler. The catalysts of the invention can also be employed in fixed bed catalytic reactions. Spent catalyst residues may be treated to recover the platinum and rhodium contents.

was followed by gas-liquid chromatography; no external heat being supplied. The time taken for the reaction to reach 85% completion (85% theoretical yield of product) was noted. Recovery of the catalyst solid from the reaction mixture was then carried out by filtration and the recovered catalyst used again in the reaction between $(Me_3SiO)_2SiMeH$ and $CH_2=CH(CH_2)_7CH_3$, the latter two reactants being employed in the same amounts as in the first run.

The procedure was repeated until 10 runs had been completed, the reaction times obtained being set out in the following table.

Also included in the table are values for comparative experiments carried out employing as catalyst chloroplatinic acid, platinum on silica and platinum on charcoal, the two latter being commercially available heterogeneous catalysts.

| Catalyst | | RUN NUMBER | | | | | | | | | |
|---|---|---|---|---|---|---|---|---|---|---|---|
| | | 1 | 2 | 3 | 4 | 5 | 6 | 7 | 8 | 9 | 10 |
| Catalyst of Invention | Temp. °C | 20 | 20 | 20 | 20 | 20 | 20 | 20 | 20 | 20 | 20 |
| | Time Min. | 107 | 15 | 17 | 21 | 23 | 40 | 38 | 47 | 50 | >90 |
| Pt on silica | Temp. °C | 20 | 20 | 20 | — | — | — | — | — | — | — |
| | Time min. | 13 | >45 | 240 | — | — | — | — | — | — | — |
| Pt on carbon | Temp. °C | 20 | 20 | 20 | — | — | — | — | — | — | — |
| | Time min. | 6 | 35 | 120 | — | — | — | — | — | — | — |
| $H_2PtCl_6 \cdot H_2O$ | Temp. °C | 20 | No recovery | — | — | — | — | — | — | — | — |
| | Time min. | 19 | possible | — | — | — | — | — | — | — | — |

The following Examples illustrate the invention:

EXAMPLE 1.

Silica gel (Grace ID 113) (5.0 g.) having a bulk density of 25 lb./cu.ft. and surface area of 400 m²/g. and $(EtSCH_2CH_2SiMe_2)_2NH$ (25.3 g.) were placed in a flask fitted with a reflux condenser and heated together for 20 hours at 140° – 150° C. The silica gel was then recovered by filtration, washed with xylene, extracted in a Soxhlet for 6 hrs. in hexane and dried at 80° C under reduced pressure to leave a granular solid having a sulphur content of 3.79% by weight.

A portion of the treated silica gel (3.79 g), $Na_2PtCl_4\cdot 4H_2O$ (0.795 g.), water (8 ml.) and ethyl alcohol (4 ml.) were shaken together for 16 hours at 20° C. The mixture was then filtered washed with $H_2O$ (8 × 10 ml.), ethyl alcohol (3 × 10 ml.) and diethyl ether (3 × 10 ml.) and dried at 20° C/10 mm.Hg for 8 hours. The product was an orange-yellow solid containing 10.05% by weight of platinum.

The effectiveness of this solid as a hydrosilylation catalyst and its ability to retain its catalytic activity on recycling were determined as follows. $(Me_3SiO)_2SiMeH$ (5.55 g.) and $CH_2=CH(CH_2)_7CH_3$ (3.5g.) were placed in a flask at 20° C together with 0.0048 g. of the orange-yellow solid prepared as described above. An exothermic reaction occurred the progress of which

EXAMPLE 2.

Silica gel (J. Crossfield U 30) (4.0 g.) having a bulk density of 26–30 lb./cu.ft. and a surface area of 500 ± 50 m²/g, $(MeO)_3Si(CH_2)_2SEt$ (4.2g.), xylene (120 ml.) and p-toluene sulphonic acid (0.2 g.) as catalyst were heated together under reflux for 13 hours at 140° C. The silica gel was then recovered by filtration, washed with xylene and then toluene and dried at 70° C under reduced pressure to yield a product having a sulphur content of 4.2% by weight.

A portion of the treated silica gel (2.19 g.), $Na_2PtCl_4\cdot 4H_2O$ (0.65 g.), water (7 ml.) and ethyl alcohol (5 ml.) were shaken together for 16 hours at 20° C. The silica gel was then recovered, washed and dried as described in Example 1 to yield a solid containing 10.42% by weight of Pt.

The effectiveness of the treated solid as a hydrosilylation catalyst was determined by employing it (0.0701 g.) in the reaction between $Cl_2MeSiH$ (47.47 g.) and $CH_2=CHCH_2Cl$ (28.68 g.). The reaction was carried out in the absence of solvent for 15 hours during which the temperature was allowed to rise from about 40 to about 80° C. The product was obtained in 50.4% yield as determined by G.L.C.

EXAMPLE 3.

Employing the procedure described in Example 1 silica gel (ID 113) (50 g.) and $(EtSCH_2CH_2SiMe_2)_2NH$ (63.59 g.) were reacted in 70 ml. AR xylene to produce a granular solid containing 3.70% by weight of sulphur. This product (2.43 g.) was then reacted with $PtCl_2$ (0.44 g.) to yield 2.01% g. of a solid containing 1.61% by weight of Pt.

The solid was then employed as a catalyst in the reaction between methyl-dichlorosilane and allyl chloride using the procedure and proportions described in Example 2. A number of runs were carried out, the catalyst being recovered and used again in the following run. After 6 runs the reaction time at 80° C for 56.2% yield of Cl₂SiMe(CH₂)₃Cl was 20¼ hours.

EXAMPLE 4.

Using the general procedure described in Example 1 silica gel (ID 113) (50 g.) was reacted with (EtSCH₂CH₂SiMe₂)₂NH (63.59 g.) to provide a solid containing 3.70% by weight of sulphur, and the product (2.16 g.) thereafter reacted with Rh(C₂H₄)₂(AcAc) (0.322 g.) to yield a solid containing 2.52% by weight of Rh.

This solid (0.0203 g.) was employed as a catalyst in the reaction between (Me₃SiO)₂SiMeH (2.22 g.) and 1-decene (1.4 g.) the reaction being followed by gas-liquid chromatography. After the first run (70 seconds at 80° – 123° C) the catalyst was recovered and employed in a second run (40 seconds at 80° – 123° C). The yield of the adduct in each run was greater than 80%.

EXAMPLE 5.

Using the procedure of Example 1 a solid carrier was prepared from silica gel (ID 113) (20 g.) and (EtSCH₂CH₂SiMe₂)₂NH (4.24 g.). This carrier (3.5 g.) and Na₂PtCl₄·4H₂O (0.57 g.) yielded a product which contained 5.8% by weight of Pt.

This Pt-containing product (0.1681 g.) was employed to catalyse the reaction between Me₃SiO(Me₂SiO)₁₄(MeHSiO)₂SiMe₃ (36.25 g.) and CH₂=CH°CH₂(OCH₂CH₂)₁₁OH (33.05 g.). The reaction was carried out in the presence of a solvent which was a mixture of equal weights of isopropyl alcohol and toluene, the solvent comprising 60% of the total weight of the reaction mixture. A number of preparative runs were carried out, the catalyst recovered after a run being employed in the following run. The reaction time for the tenth run was 15 minutes, approximately the same as that for the first run (13½ min.)

That which is claimed is:

1. As a composition of matter an inorganic particulate solid having chemically bonded to the surface thereof at least one group of the general formula

wherein the R substituents are the same or different and are selected from the group consisting of a chlorine atom, a bromine atom, a monovalent radical having from 1 to 8 inclusive carbon atoms and free of aliphatic unsaturation which is a hydrocarbon radical, a halogenated hydrocarbon radical, an oxyhydrocarbon radical, an oxime radical having less than 14 carbon atoms, an oxygen atom and the radical —NQ₂, in which each Q represents a hydrogen atom or an alkyl or an aryl radical having less than 10 carbon atoms, R' represents a divalent hydrocarbon radical having from 1 to 16 inclusive carbon atoms, R'' and R''' represents a monovalent hydrocarbon radical free of aliphatic unsaturation and having from 1 to 8 inclusive carbon atoms and $n$ is 0 or an integer of 1 to 20, the sulfur atom in said group being coordinatively bonded to an atom of platinum or rhodium.

2. A composition as claimed in claim 1 wherein the inorganic particulate solid is silica.

3. A composition as claimed in claim 2 wherein in the general formula R' has from 2 to 4 carbon atoms and $n$ is zero.

4. A process for the preparation of a composition as claimed in claim 1 which comprises reacting an inorganic particulate solid having hydroxyl groups at the surface thereof with an organosilicon compound of the general formula

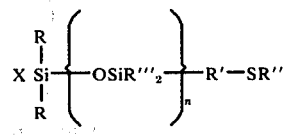

wherein R', R'', R''' and $n$ are as defined in claim 1, X represents an atom or group reactive with the surface hydroxyl groups of the inorganic particulate solid and each R is selected from the group consisting of a chlorine atom, a bromine atom, a monovalent radical having from 1 to 8 inclusive carbon atoms and free of aliphatic unsaturation which is a hydrocarbon radical, a halogenated hydrocarbon radical, an oxyhydrocarbon radical, an oxime radical having less than 14 carbon atoms and the radical —NQ₂, in which each Q represents a hydrogen atom or an alkyl or aryl radical having less than 10 carbon atoms and thereafter reacting the product with a compound or complex of platinum or rhodium having a labile ligand.

5. A process for the preparation of a composition as claimed in claim 1 which comprises reacting an inorganic particulate solid having hydroxyl groups at the surface thereof with a disilazane of the general formula

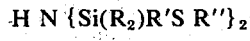

wherein R' and R'' are as defined in claim 1 and each R represents a monovalent radical having from 1 to 8 inclusive carbon atoms and free of aliphatic unsaturation which is a hydrocarbon radical, a halogenated hydrocarbon radical or an oxyhydrocarbon radical.

6. A process as claimed in claim 5 wherein the inorganic particulate solid is silica.

* * * * *

UNITED STATES PATENT AND TRADEMARK OFFICE
CERTIFICATE OF CORRECTION

PATENT NO. : 4,005,046

DATED : January 25, 1977

INVENTOR(S) : GRISH CHANDRA ET AL

It is certified that error appears in the above-identified patent and that said Letters Patent are hereby corrected as shown below:

Column 1, first formula, should read

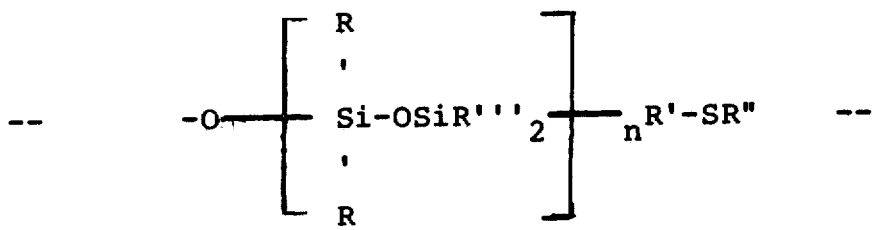

Column 1, second formula, should read

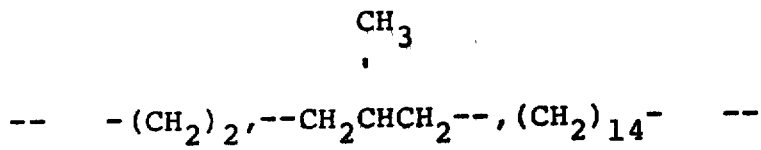

Column 6, table, first column, "$H_2PtCl_6 \cdot H_2O$" should read

UNITED STATES PATENT AND TRADEMARK OFFICE
CERTIFICATE OF CORRECTION

PATENT NO. : 4,005,046
DATED : January 25, 1977
INVENTOR(S) : Grish Chandra et al.

It is certified that error appears in the above—identified patent and that said Letters Patent is hereby corrected as shown below:

$$-- H_2PtCl_6 \cdot 6H_2O --.$$

Signed and Sealed this

Tenth Day of June 1980

[SEAL]

Attest:

SIDNEY A. DIAMOND

Attesting Officer

Commissioner of Patents and Trademarks